(12) United States Patent
Nardi et al.

(10) Patent No.: US 8,562,549 B2
(45) Date of Patent: Oct. 22, 2013

(54) COMPRESSION DEVICE HAVING AN INFLATABLE MEMBER INCLUDING A FRAME MEMBER

(75) Inventors: Steven Nardi, Taunton, MA (US); Malcolm G. Bock, Medfield, MA (US)

(73) Assignee: Covidien LP, Mansfield, MA (US)

( * ) Notice: Subject to any disclaimer, the term of this patent is extended or adjusted under 35 U.S.C. 154(b) by 1322 days.

(21) Appl. No.: 12/041,933

(22) Filed: Mar. 4, 2008

(65) Prior Publication Data

US 2009/0227919 A1    Sep. 10, 2009

(51) Int. Cl.
*A61H 7/00* (2006.01)
*A61H 19/00* (2006.01)
*A61F 5/00* (2006.01)

(52) U.S. Cl.
USPC ............................................. 601/151; 602/13

(58) Field of Classification Search
USPC ............. 601/148–152; 602/13; 606/201, 202; 36/29, 35 B, 93, 153; 441/1, 30, 40
See application file for complete search history.

(56) References Cited

U.S. PATENT DOCUMENTS

| | | | |
|---|---|---|---|
| 1,629,108 A * | 5/1927 | Lake | 601/152 |
| 1,646,590 A | 10/1927 | Mildenberg | |
| 1,976,656 A | 10/1934 | Clark | |
| 2,037,230 A * | 4/1936 | Hack | 36/29 |
| 2,183,277 A | 12/1939 | Heilhecker | |
| 2,211,057 A | 8/1940 | Duckoff | |
| 2,605,560 A * | 8/1952 | Gouabault | 36/29 |
| 2,694,395 A * | 11/1954 | Brown | 601/151 |
| 3,631,854 A * | 1/1972 | Fryer | 602/8 |
| 3,786,805 A | 1/1974 | Tourin | |
| 3,929,140 A | 12/1975 | Wesberg | |
| 3,985,853 A | 10/1976 | Weisberg | |
| 4,013,069 A | 3/1977 | Hasty | |
| 4,029,087 A | 6/1977 | Dye et al. | |
| 4,030,488 A | 6/1977 | Hasty | |
| 4,059,910 A | 11/1977 | Bryden et al. | |
| 4,187,620 A | 2/1980 | Selner | |
| 4,299,213 A * | 11/1981 | Violet | 128/882 |
| 4,476,638 A | 10/1984 | Quacquarini et al. | |
| 4,696,289 A | 9/1987 | Gardner et al. | |
| 4,721,101 A | 1/1988 | Gardner et al. | |
| 4,741,086 A * | 5/1988 | Orndorff, Jr. | 29/423 |
| 4,779,361 A | 10/1988 | Kinsaul | |
| 4,805,601 A * | 2/1989 | Eischen, Sr. | 601/151 |
| RE32,939 E | 6/1989 | Gardner et al. | |

(Continued)

FOREIGN PATENT DOCUMENTS

| | | |
|---|---|---|
| EP | 1795167 A1 | 6/2007 |
| JP | 11-197201 A | 7/1999 |
| WO | 2006065225 A1 | 6/2006 |

OTHER PUBLICATIONS

Extended European Search Report issued in Application No. 09154291.0, dated May 13, 2009, 8 pages.

*Primary Examiner* — Justine Yu
*Assistant Examiner* — Raymond G Chen
(74) *Attorney, Agent, or Firm* — John Paul Mello, Esq.

(57) ABSTRACT

A compression device includes an inflatable member and a frame member extending along substantially an entirety of the perimeter edge margin of the inflatable member. The frame member imparts rigidity to the inflatable member so that rigidity of the inflatable member at the perimeter edge margin is greater than the rigidity of the inflatable member inside the perimeter edge margin.

13 Claims, 14 Drawing Sheets

(56) References Cited

U.S. PATENT DOCUMENTS

| | | | |
|---|---|---|---|
| RE32,940 E | | 6/1989 | Gardner et al. |
| 4,887,369 A | | 12/1989 | Bailey et al. |
| 4,945,905 A | * | 8/1990 | Dye et al. ................ 601/152 |
| 4,979,953 A | * | 12/1990 | Spence .................... 606/202 |
| 5,199,191 A | | 4/1993 | Moumdjian |
| 5,201,758 A | * | 4/1993 | Glover .................... 606/202 |
| 5,321,901 A | | 6/1994 | Kelly |
| 5,345,260 A | | 9/1994 | Petralia |
| 5,354,260 A | | 10/1994 | Cook |
| 5,407,421 A | | 4/1995 | Goldsmith |
| 5,450,858 A | * | 9/1995 | Zablotsky et al. ........ 128/876 |
| 5,462,517 A | | 10/1995 | Mann |
| 5,464,385 A | | 11/1995 | Grim |
| 5,626,556 A | | 5/1997 | Tobler et al. |
| 5,651,196 A | | 7/1997 | Hsieh |
| 5,718,669 A | | 2/1998 | Marble |
| 5,741,295 A | * | 4/1998 | McEwen .................. 606/202 |
| 5,795,312 A | | 8/1998 | Dye |
| 5,848,482 A | | 12/1998 | Bathum |
| 5,848,982 A | * | 12/1998 | Hoshino et al. ........ 601/150 |
| 5,931,797 A | | 8/1999 | Tumey et al. |
| 5,954,676 A | | 9/1999 | Kramer, III |
| 5,989,204 A | | 11/1999 | Lina |
| 6,014,823 A | | 1/2000 | Lakic |
| 6,098,313 A | | 8/2000 | Skaja |
| 6,231,532 B1 | | 5/2001 | Watson et al. |
| 6,319,215 B1 | | 11/2001 | Manor et al. |
| 6,358,219 B1 | | 3/2002 | Arkans |
| 6,457,263 B1 | | 10/2002 | Rudy |
| 6,585,669 B2 | | 7/2003 | Manor et al. |
| 6,592,534 B1 | | 7/2003 | Rutt et al. |
| 6,629,942 B1 | | 10/2003 | Tubbs |
| 6,656,141 B1 | | 12/2003 | Reid |
| 6,659,838 B1 | * | 12/2003 | Anderson ................. 446/220 |
| 6,665,958 B2 | * | 12/2003 | Goodwin .................... 36/29 |
| 6,685,661 B2 | | 2/2004 | Peled |
| 6,715,218 B2 | | 4/2004 | Johnson |
| 6,736,787 B1 | | 5/2004 | McEwen et al. |
| 6,754,982 B2 | * | 6/2004 | Reed et al. ............... 36/30 A |
| 6,865,823 B1 | * | 3/2005 | Vindriis ..................... 36/29 |
| 6,945,944 B2 | | 9/2005 | Kuiper et al. |
| 6,990,755 B2 | | 1/2006 | Hatfield et al. |
| 7,100,307 B2 | | 9/2006 | Burke et al. |
| 7,225,491 B2 | * | 6/2007 | Reed et al. ............... 12/142 P |
| 7,246,453 B2 | | 7/2007 | Kim |
| 7,452,340 B2 | | 11/2008 | Cook et al. |
| 7,614,638 B2 | | 11/2009 | Cunningham et al. |
| 2001/0018564 A1 | | 8/2001 | Manor et al. |
| 2003/0036771 A1 | * | 2/2003 | McEwen et al. ........ 606/202 |
| 2004/0064976 A1 | | 4/2004 | Barteet |
| 2005/0143682 A1 | | 6/2005 | Cook et al. |
| 2007/0282233 A1 | | 12/2007 | Meyer et al. |
| 2009/0227917 A1 | | 9/2009 | Nardi |
| 2009/0227918 A1 | | 9/2009 | Nardi et al. |
| 2009/0227920 A1 | | 9/2009 | Nardi et al. |
| 2009/0227921 A1 | | 9/2009 | Nardi |
| 2009/0227922 A1 | | 9/2009 | Nardi et al. |

* cited by examiner

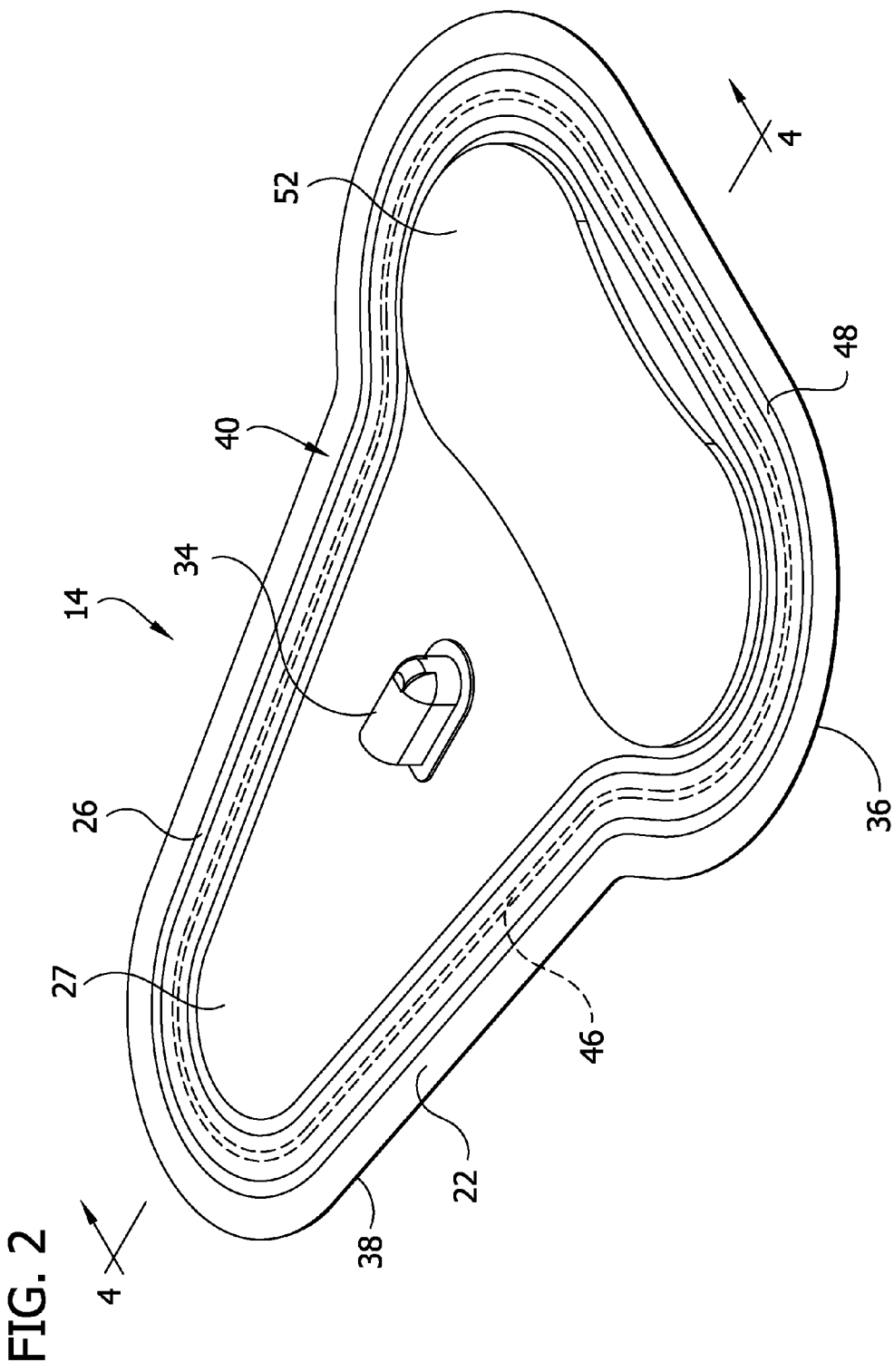

COMPRESSION DEVICE HAVING AN INFLATABLE MEMBER INCLUDING A FRAME MEMBER

FIELD OF THE INVENTION

The present invention generally relates to a sole for a compression foot cuff, and more particularly to such a sole with an anchor.

BACKGROUND

Compression devices for applying compressive forces to a selected area of a wearer's anatomy are generally employed to improve blood flow in the selected area. Compression devices that provide intermittent pulses of a compressed fluid (i.e. air) to inflate at least one inflatable chamber in a cuff or sleeve are particularly useful. This cyclic application of pressure provides a non-invasive method of prophylaxis to reduce the incidence of deep vein thrombosis (DVT), and the like. These compression devices find particular use during surgery on patients with high-risk conditions such as obesity, advanced age, malignancy, or prior thromboembolism. Patients who develop this condition often have swelling (edema) and tissue breakdown (venous stasis ulcer) in the lower leg. When a DVT occurs, the valves that are located within the veins of the leg can be damaged, which in turn can cause stasis and high pressure in the veins of the lower leg.

Generally, these compression devices are fluidly coupled to a source of pressurized fluid by one or more air tubes. Additionally, each compression device includes a flexible shell having one or more bladders disposed therein. The compression device is placed around the patient's foot or other selected portion whereupon a pressurized fluid is delivered into the bladder creating pressure at the part or parts of the body in contact with the bladder.

Compression cuffs adapted for use with a patient's foot may be used by themselves or combined with one or more additional compression cuffs or sleeves that are disposed on portions of a patient's leg for improving the treatment regimen. In general, each of the additional compression sleeves includes a plurality of separate inflatable chambers that are progressively arranged along a longitudinal axis of the sleeve from a lower portion to an upper portion of the limb. A pressure source, e.g. a controller, is provided for intermittently forming a pressure pulse within these inflatable chambers from a source of pressurized fluid during periodic compression cycles. The compression sleeves provide a pressure gradient along the patient's limbs during these compression cycles which progressively decreases from the lower portion to the upper portion of the limb (e.g. from the ankle to the thigh).

Compression cuffs that are adapted for use with a patient's foot generally include a heel strap with a tab portion that is adapted to fit around a portion of the patient's heel. This arrangement allows the compression cuff to be wrapped around and releasably attached to the patient's foot. The compression cuff may include a generally rigid sole to direct expansion of the inflatable chamber toward the wearer's foot. The rigid sole needs to be located under that portion of the inflatable member that is acting on the portion of the foot to produce blood flow out of the foot. Conventionally, the rigid sole is temporarily attached to the bladder by double stick tape. Final location and positioning of the rigid sole may be carried out by stitching. For example, the bladder is typically stitched to an outer wrap of the foot cuff. The stitching can be arranged so that it captures the rigid sole in position relative to the bladder, as well as the outer wrap. This requires care and precision in manufacturing the foot cuff.

Examples of compression cuffs are disclosed in U.S. Pat. Nos. 4,013,069 and 4,030,488 to Hasty, U.S. Pat. Nos. 4,029,087 and 5,795,312 to Dye, U.S. Pat. No. 5,626,556 to Tobler et al., and U.S. patent application Ser. No. 11/761,212 to Meyer et al., all of which are currently owned by Tyco Healthcare Group LP and are incorporated by reference herein in their entireties. Other examples of compression cuffs are disclosed in U.S. Pat. No. 4,696,289 to Gardner et al., U.S. Pat. No. 5,989,204 to Lina and U.S. Pat. No. 5,345,260 to Cook. An example of compression treatment method is disclosed in U.S. Pat. No. 6,231,532 to Watson et al., which is owned by Tyco Healthcare Group LP, the contents of which are hereby incorporated by reference herein in their entirety.

SUMMARY

In one aspect, a compression device for applying compression to a part of a wearer's body generally comprises an inflatable member including first and second fluid impermeable layers secured to one another to define an inflatable chamber. The inflatable member has a perimeter edge margin. A frame member extends along substantially an entirety of the perimeter edge margin of the inflatable member. The frame member imparts rigidity to the inflatable member so that rigidity of the inflatable member at the perimeter edge margin is greater than the rigidity of the inflatable member inside the perimeter edge margin.

In another aspect, a foot cuff for applying compressive pressure to a foot of a wearer generally comprises an inflatable member including first and second fluid impermeable layers secured to one another to define an inflatable chamber. The inflatable member has a body portion sized and shaped to underlie the foot extending generally between the ball and the heel of the foot. A wing portion extends laterally outward from the body portion. Substantially an entirety of a perimeter edge margin of the inflatable member has a rigidity greater than a rigidity of the inflatable member inside the perimeter edge margin. The foot cuff comprises an outer cover. The inflatable member is secured to the outer cover at the wing portion of the inflatable member. The body portion of the inflatable member is free from securement to the outer cover.

In yet another aspect, a method of making a foot cuff for applying compressive forces to a foot of a wearer generally comprises rigidifying substantially an entirety of a perimeter edge margin of an inflatable member having a body portion sized and shaped to underlie the foot extending generally between the ball and the heel of the foot and a wing portion so that the inflatable member at substantially the entirety of the perimeter edge margin is more rigid than the inflatable member inside the perimeter edge margin. The inflatable member is secured to an outer cover of the foot cuff at a discrete location at the wing portion of the inflatable member.

Other features will be in part apparent and in part pointed out hereinafter.

BRIEF DESCRIPTION OF THE DRAWINGS

FIG. 2 is a perspective of the bladder of the foot cuff with a sole attached thereto;

Corresponding reference characters indicate corresponding parts throughout the drawings.

DETAILED DESCRIPTION OF THE DRAWINGS

Figure 1:
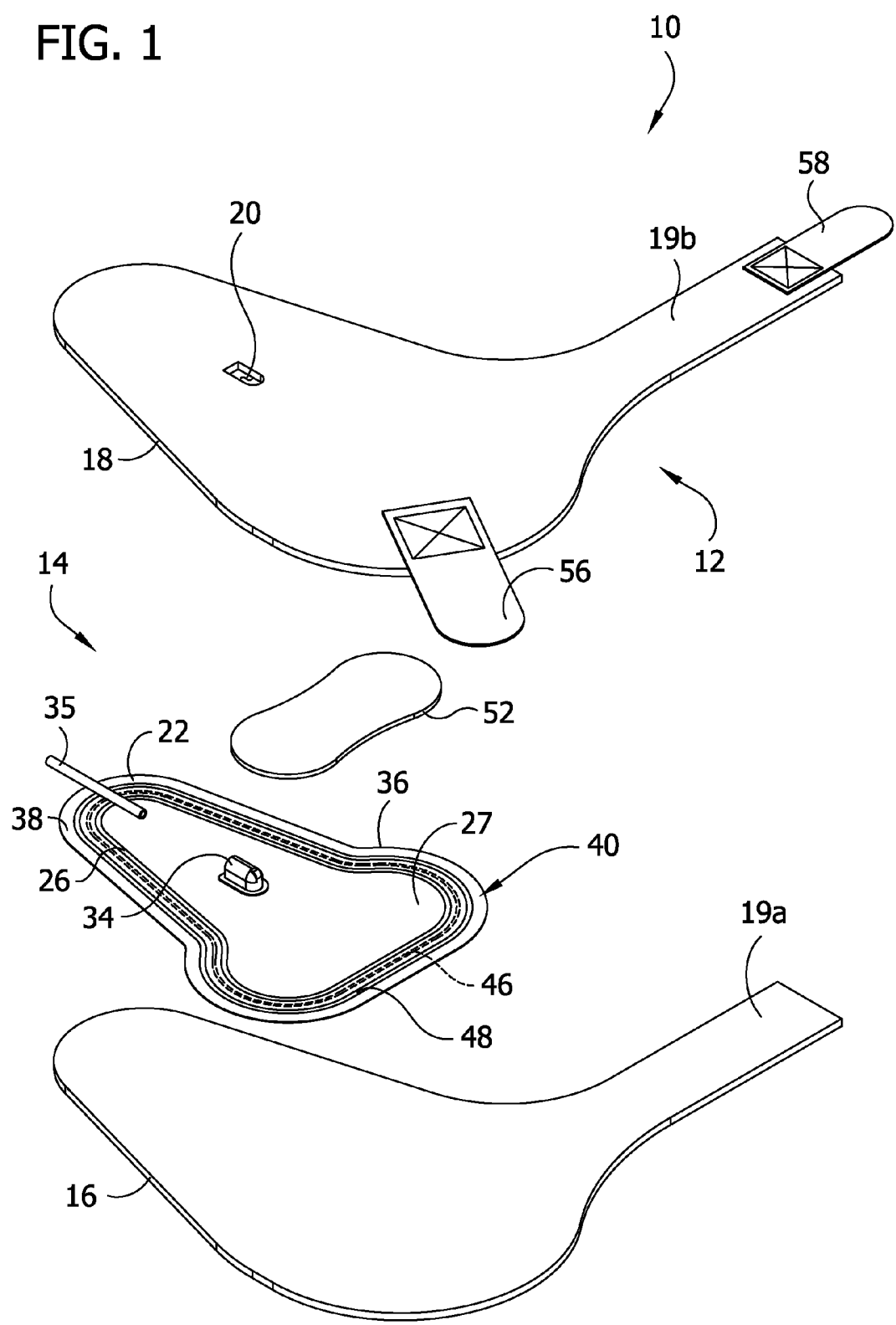
FIG. 1 is an exploded perspective of a first embodiment of a compression foot cuff in accordance with the present disclosure.

Referring now to the drawings, and in particular to FIG. 1, a compression foot cuff for applying compressive pressure to a wearer's foot is generally indicated at 10. The foot cuff is adapted for use in a compression therapy system, which further includes a supply of pressurized air (not shown) and tubing connecting the supply of pressurized air to the foot cuff.

As shown best in FIG. 1, the foot cuff 10 includes an envelope, generally indicated at 12, substantially enveloping or enclosing a bladder, generally indicated at 14. The envelope 12 includes an inner contact layer 16 and an outer layer 18 secured to one another generally adjacent to corresponding perimeters of the layers to define an interior space for receiving and substantially enclosing the bladder 14 (broadly, "an inflatable member") therein. The contact layer 16 and the outer layer 18 may be fixedly secured to one another at their peripheral edge margins, such as by heat welding, adhesives, sewing or other suitable ways. Alternatively, the contact layer 16 and the outer layer 18 may be releasably secured to one another. In use the contact layer 16 is adjacent to the wearer's foot and the outer layer 18 is located farthest from the foot. As used herein, the terms "inner" and "outer" indicate relative positions of respective components and surfaces with respect to the skin of the wearer's body part when the compression device is secured to the body part, and as such, an "inner" component or surface is more adjacent to the skin of the body part than an "outer" component or surface.

Contact layer 16 and outer layer 18 of the envelope 12 include ankle strap portions 19a and 19b respectively. Ankle strap portions 19a, 19b have a longitudinally projecting configuration for wrapping about a portion of the foot adjacent to the ankle. The ankle strap portions 19a, 19b can be sewn, RF welded, or sonic welded. However, in the illustrated embodiments, the ankle strap portions 19a, 19b are formed as one piece with the contact layer 16 and outer layer 18, respectively.

Contact layer 16 of the envelope 12 is adapted for contacting the foot. Contact layer 16 is in one embodiment fabricated from a chemically treated material, with wicking ability, for wicking away moisture from the skin. In one embodiment, contact layer 16 includes a mesh-like fabric capable of wicking moisture away from the patient's skin. Furthermore, the contact layer 16 can be faced with a soft material toward the treatment surface of the patient. For example, the material can be a thin layer of open celled porous foam, napped cloth, or a layer of vapor permeable cloth permeable. It is understood that the cuff 12 may not include a contact layer within the scope of the present invention.

Outer layer 18 of the envelope 12 includes an opening 20 for permitting a pressurized fluid inlet passage therethrough. Outer layer 18 is configured for providing the attachment surface for a hook and loop feature of cuff 12, as will be described in more detail herein below. Moreover, the outer layer 18 provides a soft material for cushioning effect against the top portion of the feet and may be fabricated from similar materials as contact layer 16 and in similar dimensions therewith for corresponding geometry. Alternatively, outer layer 18 may be fabricated from a laminated material, such as, for example, sontara fabric, open cell urethane foam, or loop fabric. It is understood that the cuff 12 may not include an outer layer within the scope of the present invention.

Referring to FIGS. 1-4, the bladder 14 is configured for positioning against the bottom portion of the foot. The bladder 14 includes outer and inner layers 22, 24 (FIGS. 3 and 4) of air impermeable material (e.g., PVC) joined together in a suitable manner along a sealing line 26 adjacent to their peripheries to define a single inflatable chamber 27. The layers 22, 24 may be joined to one another in a suitable manner such as by radio frequency (RF) welding. Other ways of joining the layers 22, 24 include sewing, adhesive, heat sealing, etc. The inflatable chamber 27 of the bladder 14 is adapted for receiving and retaining a pressurized fluid (e.g. air) for exerting compressive pressure to the foot during successive pressure application cycles. It is understood that the bladder 14 can include more than one inflatable chamber 27 within the scope of the present invention. The inflatable chamber 27 has a port or inlet member 34 and a tube 35 connected to the inlet member for air or fluid to be introduced into the chamber during the start of a compression cycle and to be exhausted to end the compression cycle. The inlet member 34 of the illustrated embodiment is a plastic component that is secured such as by heat welding or other means to the bladder 14. It is understood that other ways of introducing air or fluid into the chamber 27 are within the scope of the invention. The bladder 14 has a body portion 36 sized and shaped to underlie the foot and extend generally between the ball and the heel of the foot. A wing portion 38 of the bladder 14 extends laterally outward from the body portion 36. A perimeter edge margin of the bladder 14, generally indicated at 40, extends along the periphery of the body portion 36 and the wing portion 38.

Figure 1A:
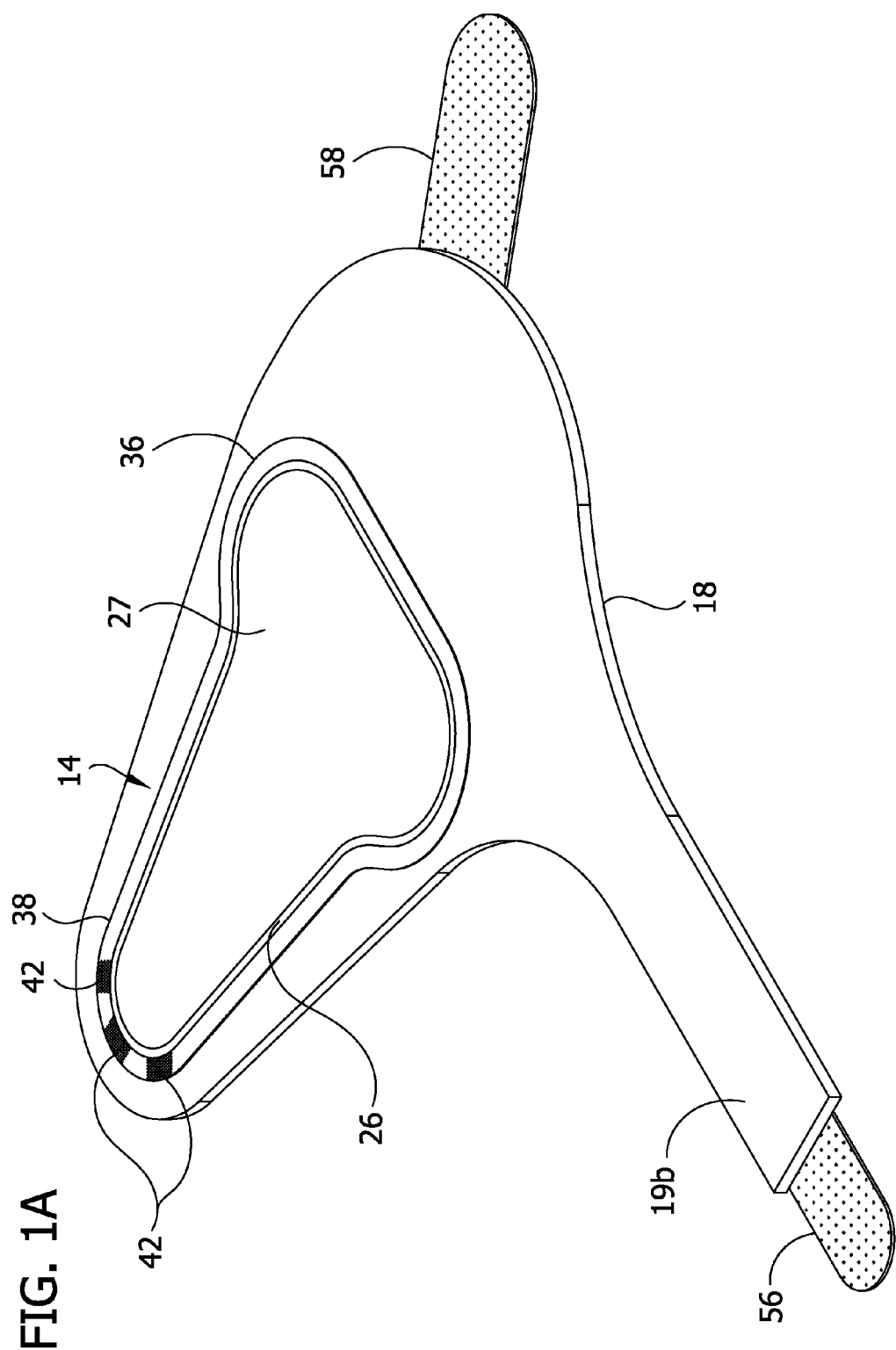
FIG. 1A is a perspective of the foot cuff with a contact layer removed to show a bladder attached to an outer layer of the foot cuff.
Figure 3:
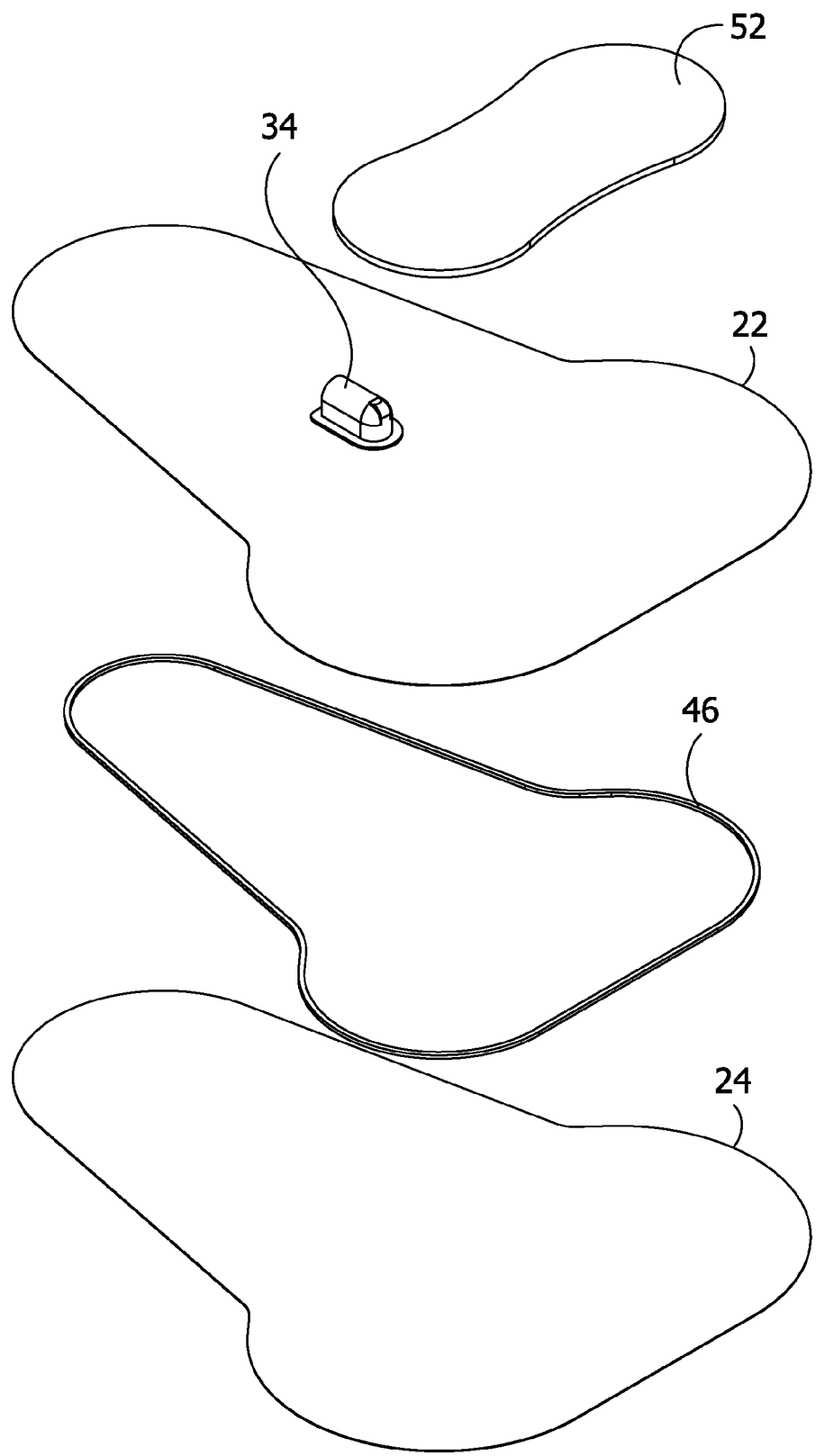
FIG. 3 is an exploded view of FIG. 2.
Figure 4:
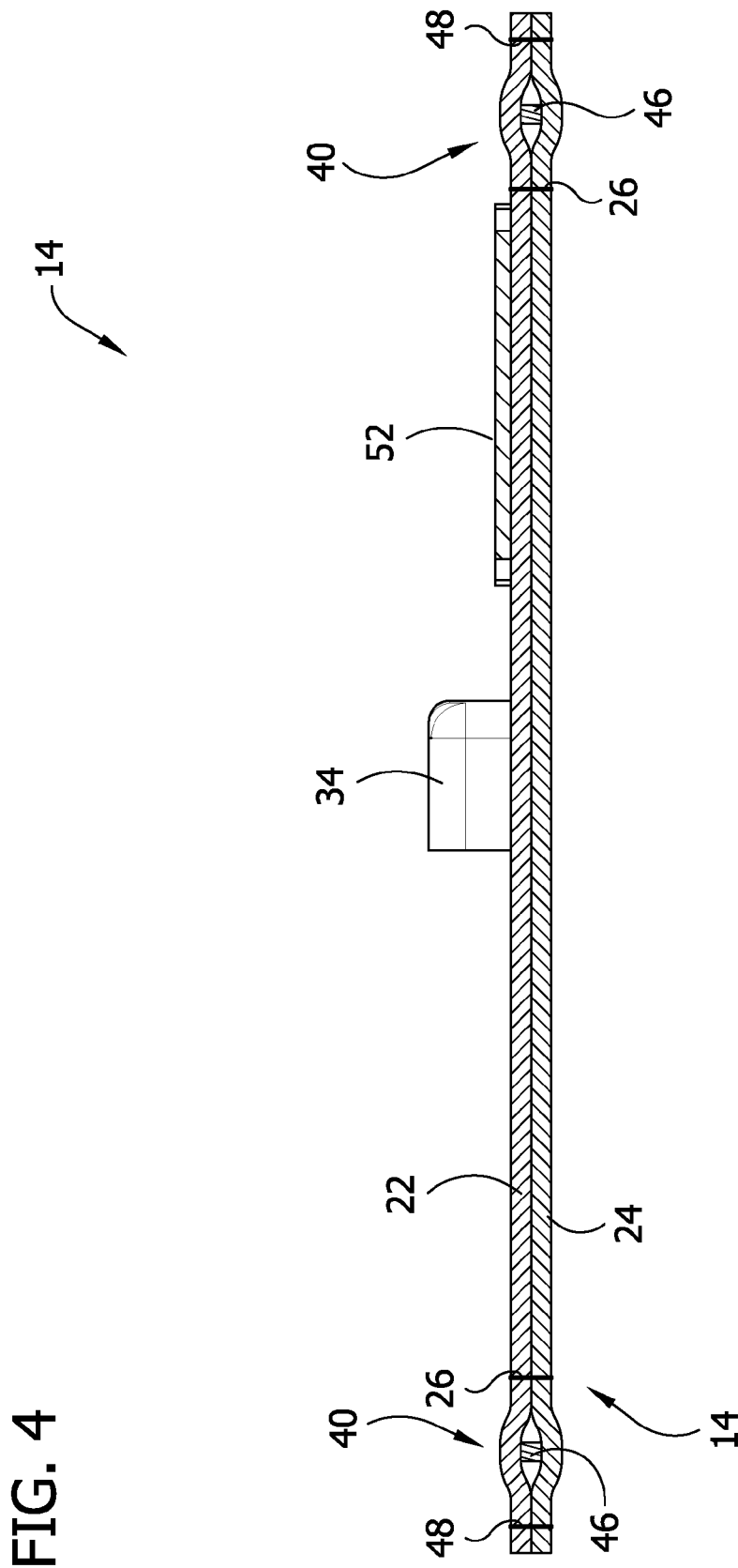
FIG. 4 is a section of the bladder with the attached sole taken along the line 4-4 in FIG. 2.

Referring to FIG. 1A, the bladder 14 is secured to the outer layer 18 of the envelope 12 at the wing portion 38 of the bladder to position the bladder relative to the outer layer of the envelope. For reasons described below, the body portion 36 of the bladder 14 is free from securement to the outer layer 18 of the envelope 12, although the body portion may be secured to the envelope within the scope of the present invention. In the illustrated embodiment (FIG. 1A), the wing portion 38 of the bladder 14 is secured to the envelope 12 at discrete locations 42 along the perimeter edge margin 40 of the bladder. As an example and without being limiting, the wing portion 38 of the bladder 14 may be secured to the envelope 12 by sewing, adhesive, heat welding or in other ways without departing from the scope of the invention. The wing portion 38 may be secured to the envelope 12 at other locations other than the perimeter edge margin 40. Moreover, the wing portion 38 may be secured along a continuous portion without departing from the scope of the invention.

Referring to FIGS. 1-4, a frame member 46 secured to the bladder 14 generally rigidifies the perimeter edge margin 40 of the bladder to retain the bladder, in particular the body portion 36 of the bladder, in its proper position relative to the outer layer 18 of the envelope 12 without the need to directly attach the body portion of the bladder to the outer layer. Accordingly, the body portion 36 of the bladder 14 may be free from securement to the envelope 12. In the first illustrated embodiment, the frame member 46 comprises a continuous strip of material secured to and extending along substantially an entirety of the perimeter edge margin 40 of the bladder 14. It is understood that the frame member 46 may be discontinuous and may not extend around the entirety of the perimeter edge margin 40 of the bladder 14 within the scope of the present invention. With particular reference to the first illustrated embodiment, the frame member 46 is secured to the bladder 14 outside the perimeter of the sealing line 26 defining the inflatable chamber 27. The frame member 46 is trapped between the outer and inner layers 22, 24 of the bladder 14 between the sealing line 26 and an outer sealing line 48. The outer sealing line may be formed by heat welding the outer and inner layer 22, 24 of the bladder to one another or on other ways without departing from the scope of the invention. Other ways of securing the frame member 46 outside the perimeter of the sealing line 26 is within the scope of the invention. The frame member 46 imparts rigidity to the bladder 14 so that the rigidity of the bladder at the perimeter edge margin 40 is greater than the rigidity of the bladder inside the perimeter edge margin. The frame 46 can be useful to prevent the bladder 14 from folding over on itself during manufacture and shipment. However, the frame 46 is preferably not so rigid as to inhibit wrapping of the cuff 10 around the foot or to produce discomfort to the wearer. In one example and without being limiting, the frame member 46 comprises a resiliently compressible foam-like material. Other types of materials are within the scope of the present invention.

A generally rigid sole 52 (broadly, a counterforce component) is disposed between the outer layer 18 of the envelope 12 and the outer layer 22 of the bladder 14. It is believed the sole 52 provides a counterforce to the outer layer 22 of the bladder 14 as the bladder is expanding to direct expansion toward the contact layer 16 and the user's foot. In this way, the inner layer 24 expands outward more than the outer layer 22 to direct compressive force toward the user's foot. The sole 52 may be constructed from a polystyrene material or other material within the scope of the invention. The sole 52 may be secured to the outer layer 18 of the envelope and/or to the outer layer 22 of the bladder 14 to fix the position of the sole relative to the bladder. For example, the sole 52 may be secured to the outer layer 18 by adhesive, heat welding, or other mechanical means. It is understood that the compression device may not have a sole within the scope of the present invention.

Referring back to FIG. 1, hook fasteners 56, 58 are provided for securing the wrapped cuff 12 around a foot, and are positioned on the outer layer 18 of the cuff. Hook fastener 56 is mounted to strap portion 19b of outer layer 18 of foot cuff 12 while hook fastener 58 is mounted on a surface of outer layer 18. In use, when ankle strap portions 19a, 19b are wrapped about the back of the foot, hook fastener 56 engages outer layer 18 to facilitate mounting of foot cuff 12 on the foot. An identification tab (not shown) may also be included for providing information such as the model number and manufacturer name. Hook fasteners 56, 58 may have tabs (not shown) without fastening material thereon to provide convenient gripping locations on the hook fasteners to thereby allow the practitioner to easily remove the hooks from the outer face of outer layer 18. The use and operation of the foot cuff 12 for applying compression therapy to the wearer's foot is generally known in the art and will not be described herein.

Figure 5:
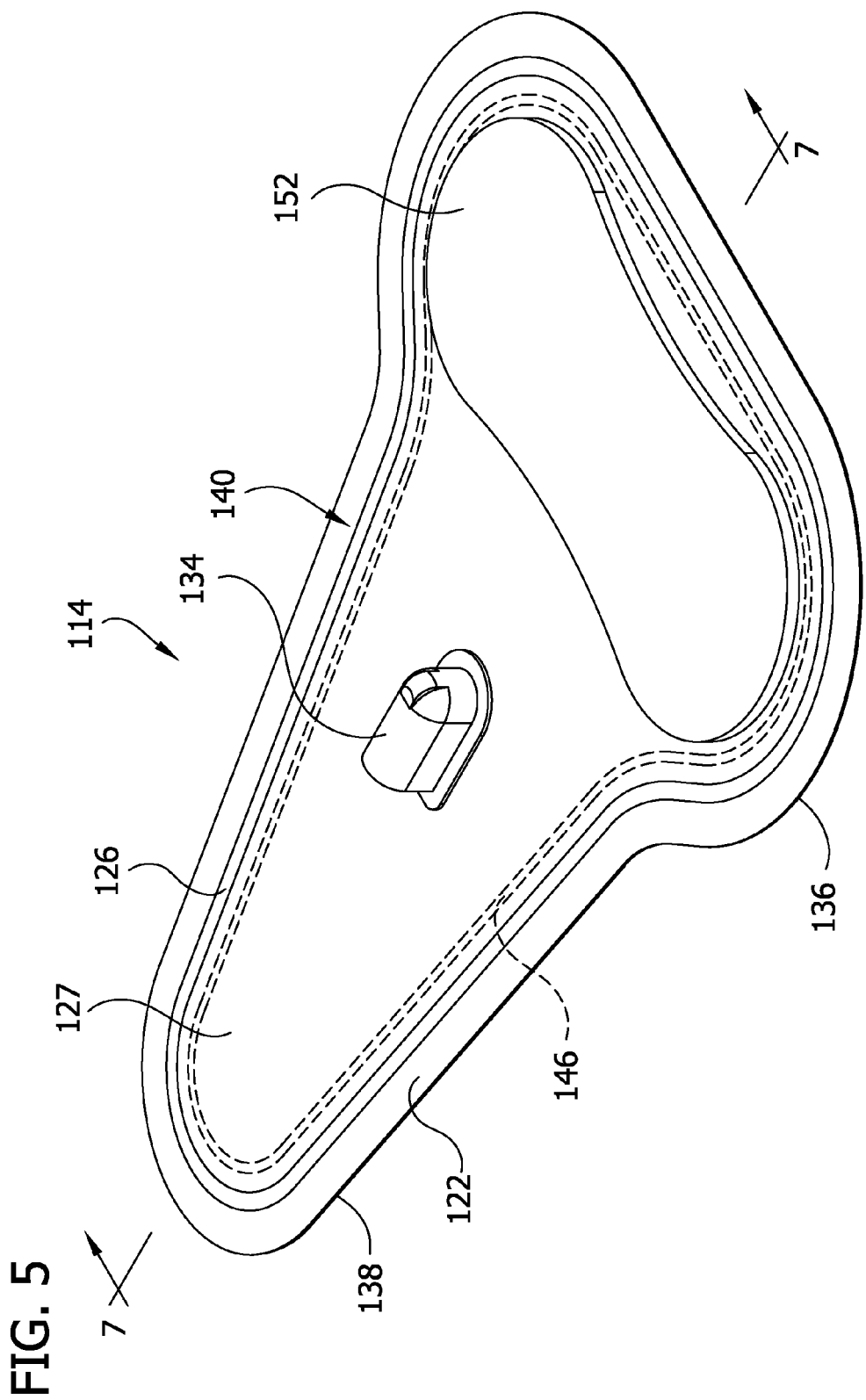
FIG. 5 is a perspective of a second embodiment of a bladder of a compression foot cuff in accordance with the present disclosure.
Figure 6:
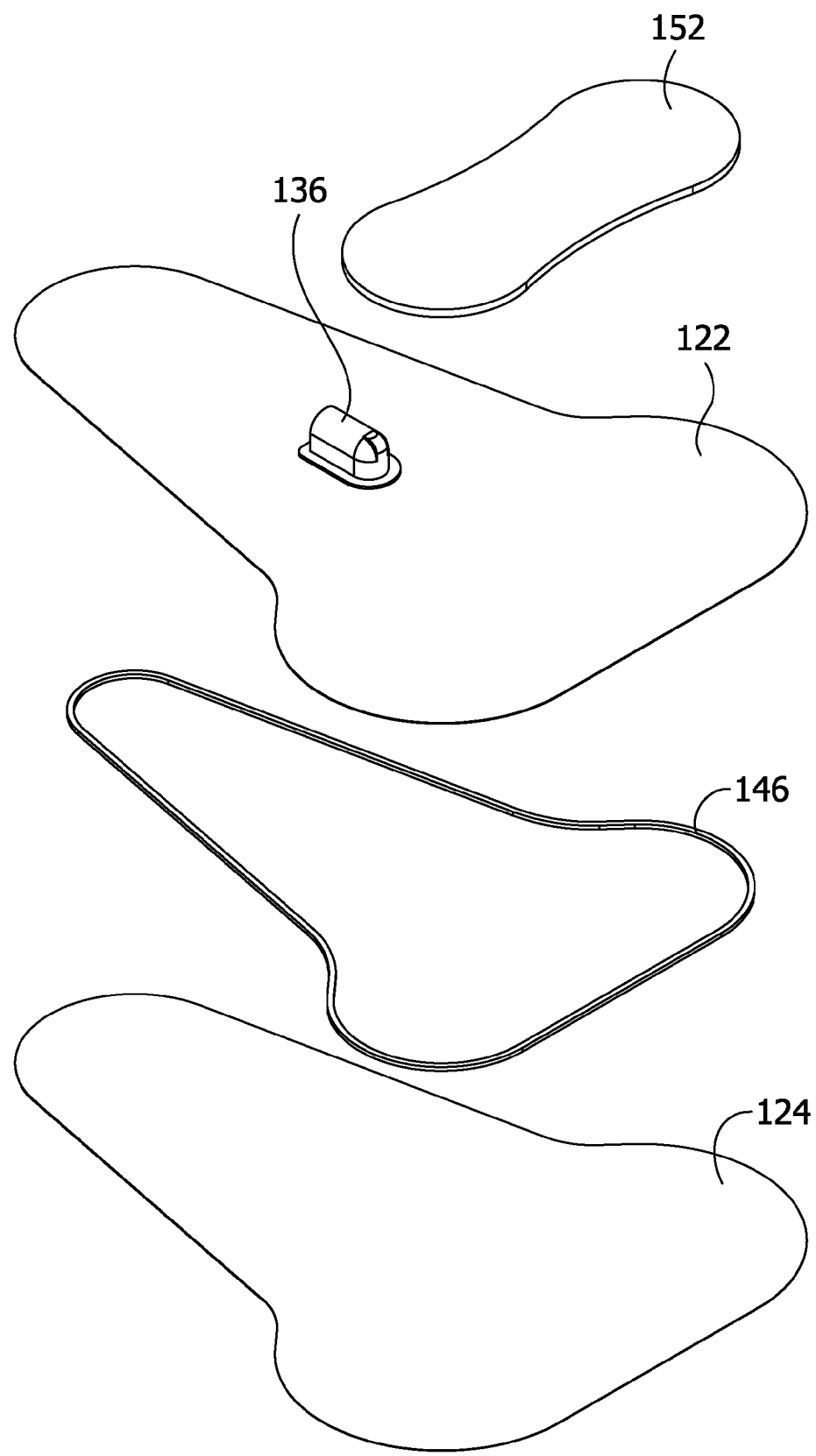
FIG. 6 is an exploded view of FIG. 5.
Figure 7:
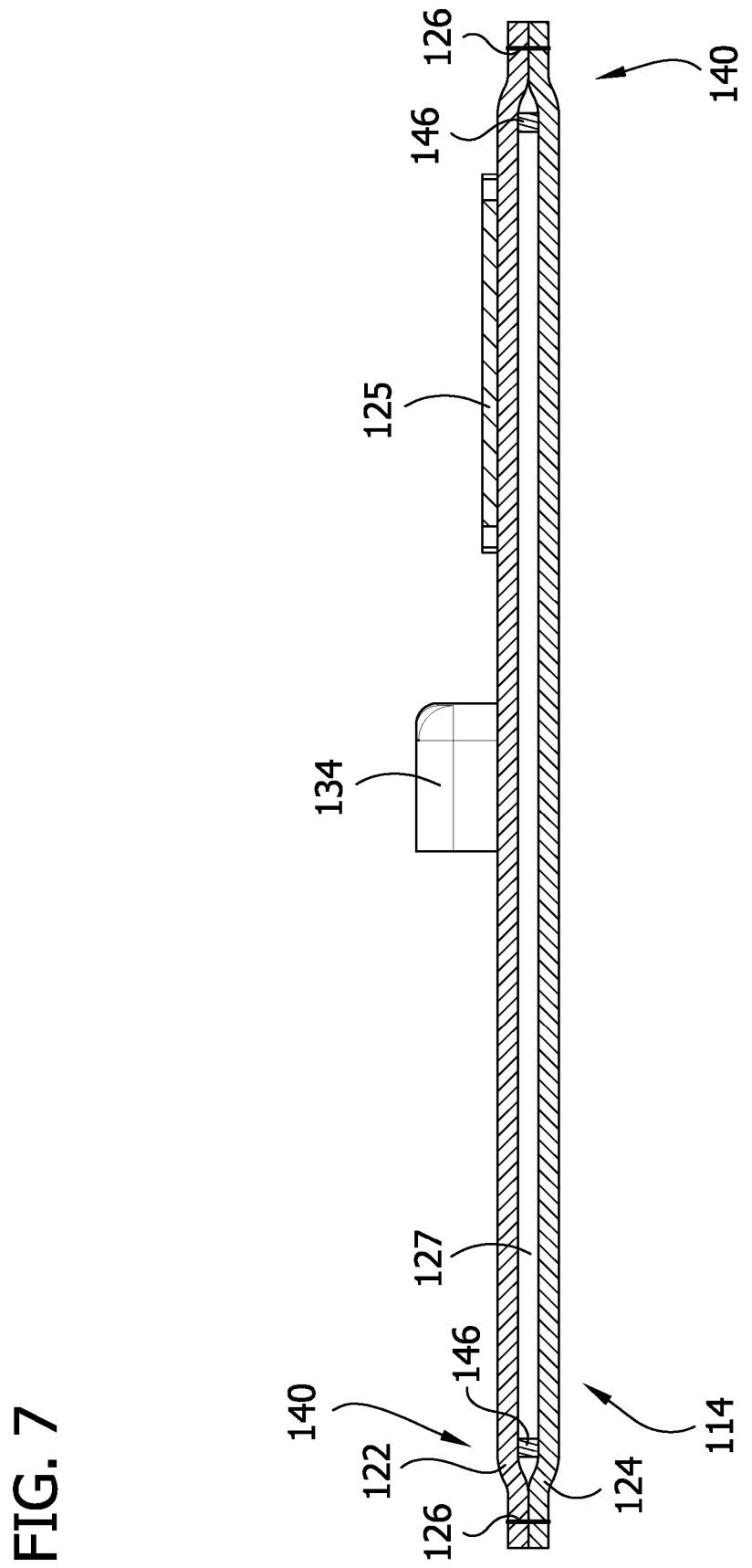
FIG. 7 is a section of the bladder with the attached sole taken along the line 7-7 in FIG. 5.

Referring to FIGS. 5-7, a second illustrated embodiment of the bladder is generally indicated at 114. This second illustrated embodiment is similar to the bladder 14 of the first illustrated embodiment, and therefore, like components will be indicated using corresponding reference numerals, plus 100. In the second illustrated embodiment, a frame member 146 is secured within the inflatable chamber 127 of the bladder 114. In this embodiment, the frame member 146 may be similar in construction to the frame member 46 of the previous embodiment with the difference being that the present frame member is sized and shaped to extend within the perimeter edge margin 140 and inside the perimeter of the sealing line 126 defining the inflatable chamber 127. As with the frame member 46 of the first illustrated embodiment, the frame member 146 of the second illustrated embodiment generally rigidifies the perimeter edge margin 140 of the bladder 114 to retain the bladder, in particular the body portion 136 of the bladder, in its proper position relative to the outer layer 118 of the envelope 112 without the need to secure the body portion of the bladder to the outer layer. The frame member 146 may be secured to one or both of the outer and inner layers 122, 124 of the bladder 114 within the inflatable chamber 127, although it is envisioned that the frame member may be retained in place within the chamber without the need to secure the frame member to one or both of the layers. It is understood that other aspects of the first illustrated embodiment, including securement of the wing portion 138 of the bladder 114 to the envelope 112, may apply equally to the second illustrated embodiment.

Figure 8:
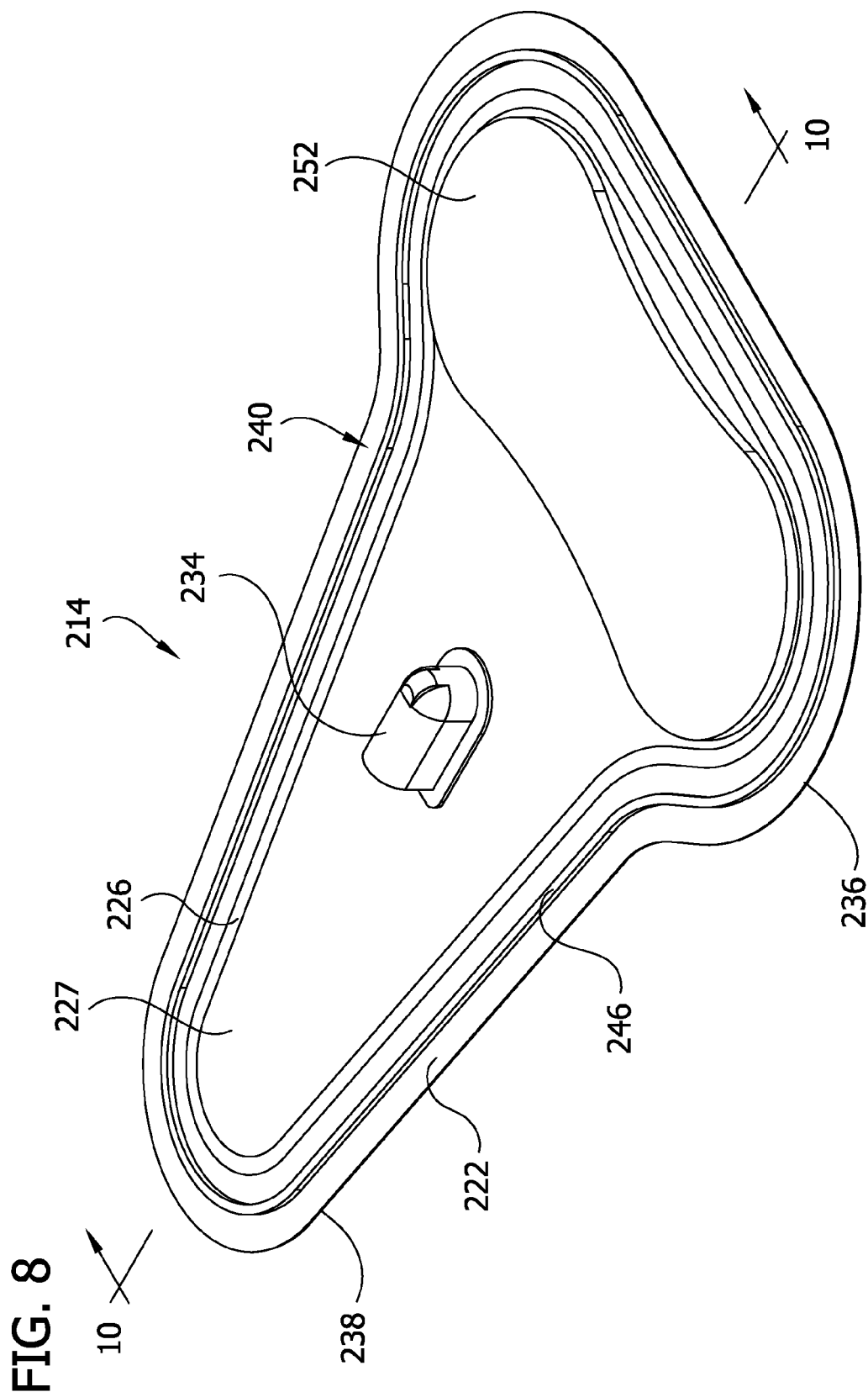
FIG. 8 is a perspective of a third embodiment of a bladder of a compression foot cuff in accordance with the present disclosure.
Figure 9:
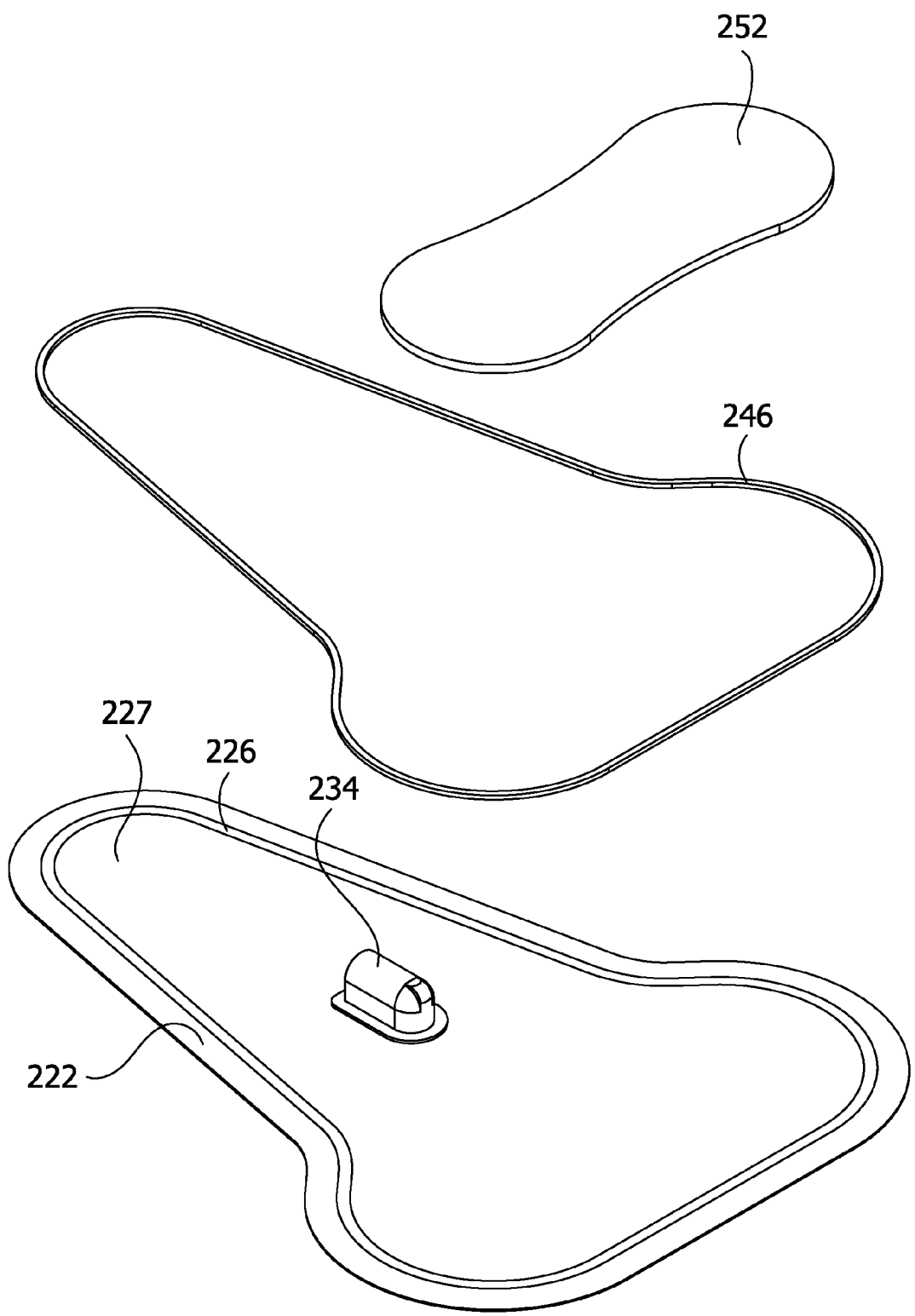
FIG. 9 is an exploded view of FIG. 8.
Figure 10:
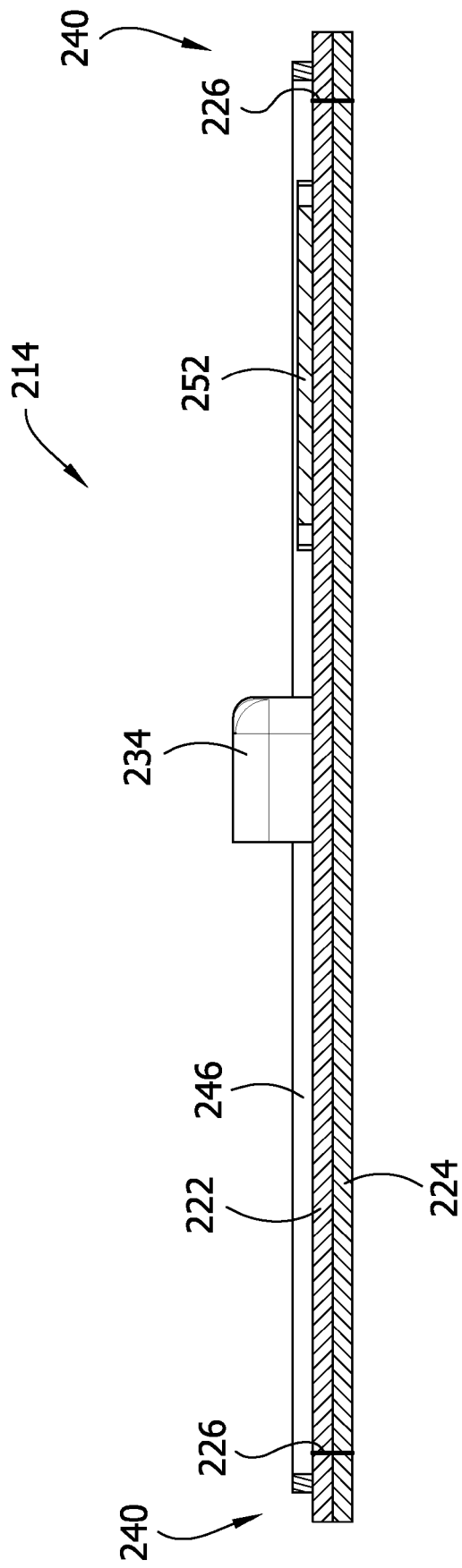
FIG. 10 is a section of the bladder with the attached sole taken along the line 10-10 in FIG. 8.

Referring to FIGS. 8-10, a third embodiment of the bladder 214 is generally indicated at 214. The third illustrated embodiment is similar to the bladder 14 first illustrated embodiment, and therefore, like components will be indicated using corresponding reference numerals, plus 200. Like the first illustrated embodiment, the third illustrated embodiment includes a sealing line 226 defining a single inflatable chamber 227, a port or inlet member 234, and a generally rigid sole 252. In the third illustrated embodiment, a frame member 246 may be similar in construction to the frame member 46 of the previous embodiment with the difference being that the present frame member is attached to an exterior surface of the bladder 214. In particular, the frame member 246 is attached to the exterior surface of the inner layer 224 of the bladder 214, although it is understood that the frame member may be attached to the exterior surface of the outer layer 222. The frame member 246 extends within the perimeter edge margin 240 of the bladder 214 and generally rigidifies the perimeter edge margin of the bladder to retain the bladder, in particular the body portion 236 of the bladder, in its proper position relative to the outer layer 218 of the envelope 212 without the need to directly attach the body portion of the bladder to the outer layer. The frame member 246 may be attached to the exterior surface of the bladder 214 by adhesive, heat welding or in other ways within the scope of the present invention. It is understood that other aspects of the first illustrated embodiment, including securement of the wing portion 238 of the bladder 214 to the envelope 212, may apply equally to the third illustrated embodiment.

Figure 11:
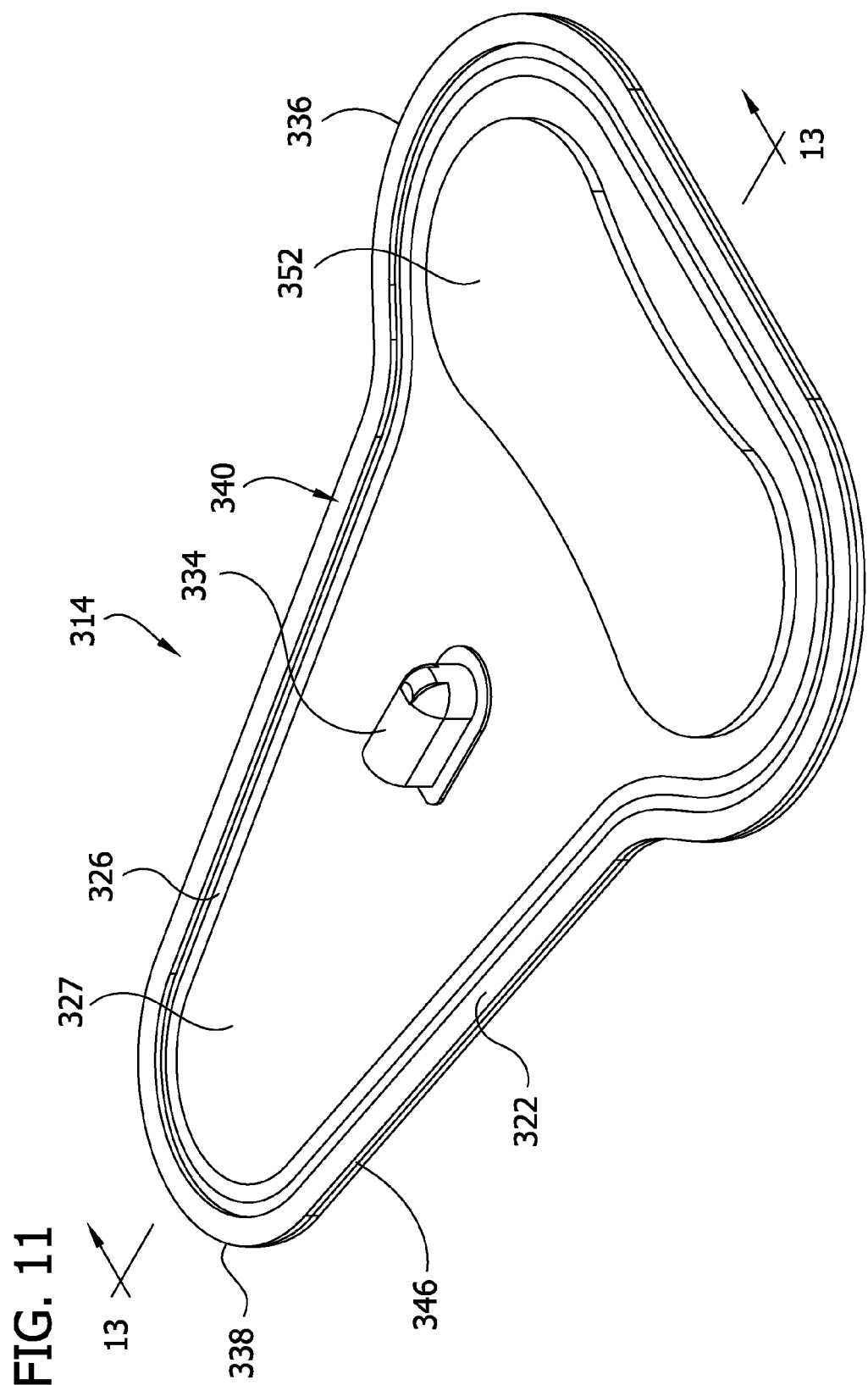
FIG. 11 is a perspective of a fourth embodiment of a bladder of a compression foot cuff in accordance with the present disclosure.
Figure 12:
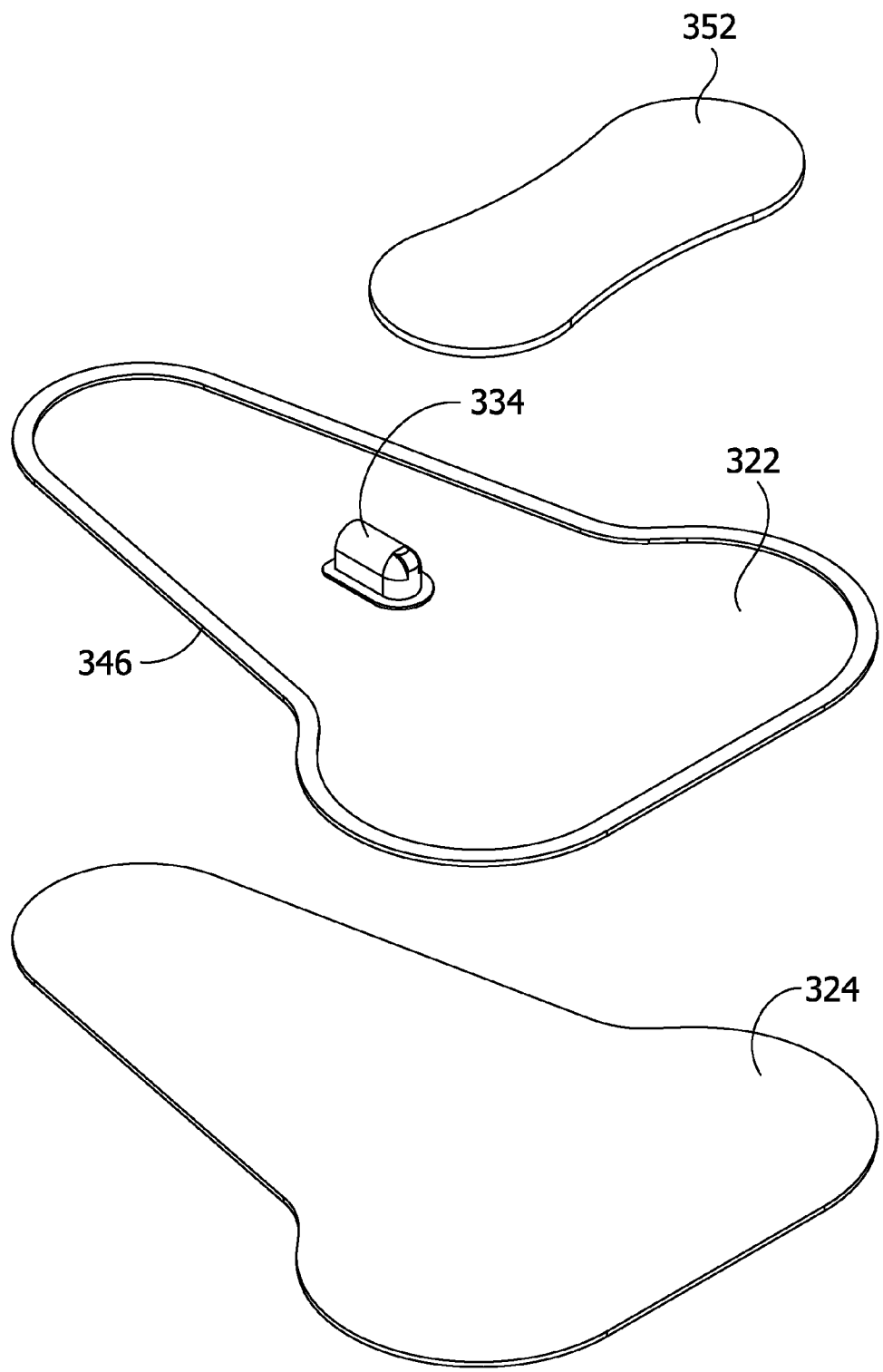
FIG. 12 is an exploded view of FIG. 11.
Figure 13:
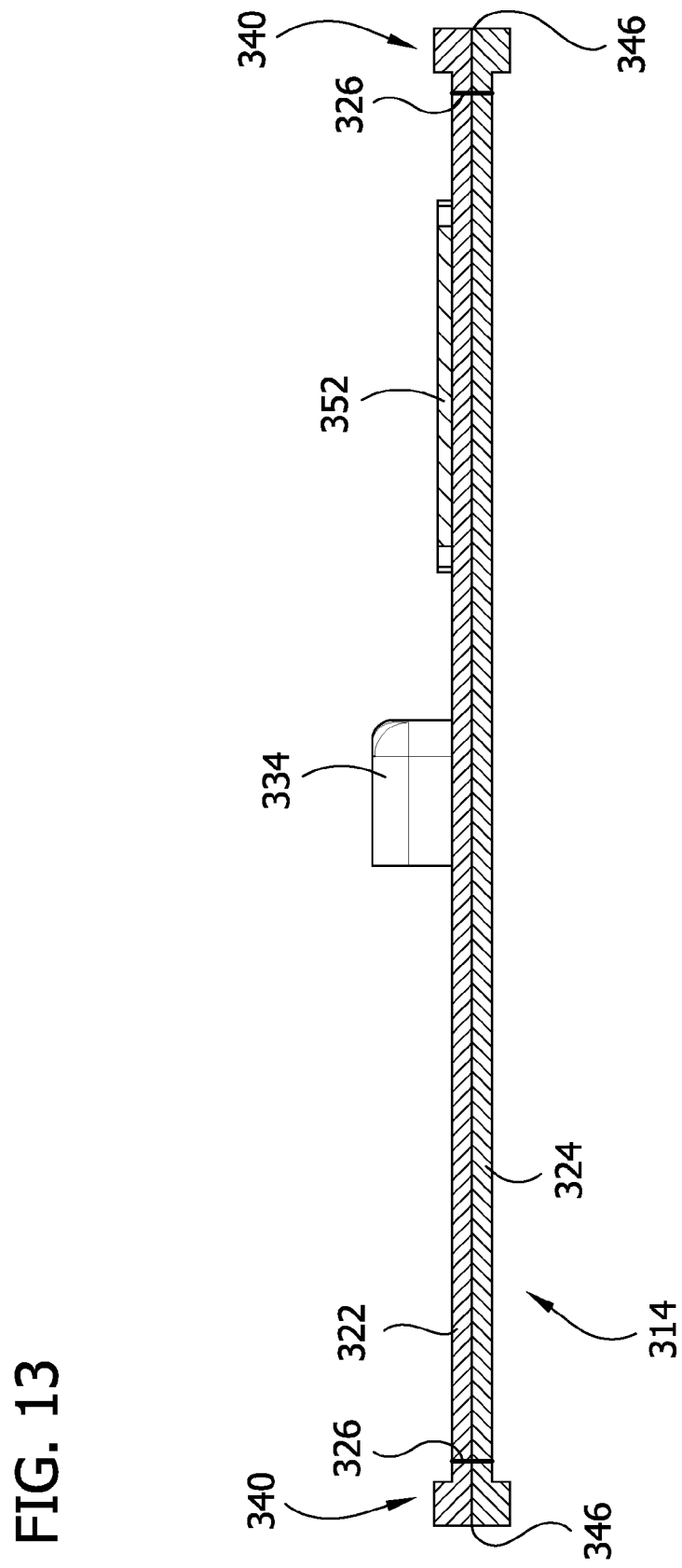
FIG. 13 is a section of the bladder with the attached sole taken along the line 13-13 in FIG. 11.

Referring to FIGS. 11-13, a fourth embodiment of the bladder is generally indicated at 314. The fourth illustrated embodiment is similar to the bladder 14 of the first illustrated embodiment, and therefore, like components will be indicated using corresponding reference numerals, plus 300. Like the first illustrated embodiment, the fourth illustrated embodiment includes a port or inlet member 334, and a generally rigid sole 352. In the fourth illustrated embodiment, the frame member 346 is formed integrally with the bladder 314. In particular, the thickness of the bladder 314 at the perimeter edge margin 340 of the bladder is greater than the thickness of the bladder inside the perimeter edge margin. By increasing the thickness of the bladder 314 at its perimeter edge margin 340, the perimeter edge margin of the bladder is generally rigidified to retain the bladder, in particular the body portion 336 of the bladder, in its proper position relative to the outer layer 318 of the envelope 312 without the need to directly attach the body portion of the bladder to the outer layer. In the illustrated embodiment, the thicknesses of both the inner layer 324 and outer layer 322 are increased at the perimeter edge margin 340, although it is understood that only one of the layers may have an increased thickness within the scope of the present invention. Moreover, the increased thickness of the bladder 314 resides outside the perimeter of the sealing line 326 defining the inflatable chamber 327, although it is understood that the increased thickness may encompass the perimeter of the sealing line and/or may reside inside the perimeter of the sealing line. It is understood that other aspects of the first illustrated embodiment, including securement of the wing portion 338 of the bladder 314 to the envelope 314, may apply equally to the fourth illustrated embodiment.

Having described the invention in detail, it will be apparent that modifications and variations are possible without departing from the scope of the invention defined in the appended claims.

When introducing elements of the present invention or the illustrated embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A compression device for applying compression to a part of a wearer's body comprising:
    an outer layer;
    an inflatable member including first and second fluid impermeable layers secured to one another to define an inflatable chamber, the inflatable member having a perimeter edge margin, wherein the inflatable member has a body portion configured to underlie a foot of the wearer and extend generally between the ball and the heel of the foot, and a wing portion extending laterally outward from the body portion, the inflatable member directly overlying the outer layer and being secured to the outer layer at the wing portion of the inflatable member, an entirety of the body portion of the inflatable member being free from direct securement to the outer layer; and
    a frame member that is a separate piece of material from the inflatable member and has a rigidity greater than a rigidity of the inflatable member, the frame member being secured to the inflatable member and extending along substantially an entirety of the perimeter edge margin of the inflatable member, the frame member imparting rigidity to the inflatable member so that rigidity of the inflatable member at the perimeter edge margin is greater than the rigidity of the inflatable member inside the perimeter edge margin.

2. A compression device as set forth in claim 1 wherein the frame member is secured between the first and second layers of the inflatable member.

3. A compression device as set forth in claim 2 wherein the first and second layers of the inflatable member are secured to one another along a sealing line having a perimeter, wherein the frame member is secured to the inflatable member outside the perimeter of the sealing line.

4. A compression device as set forth in claim 2 wherein the first and second layers of the inflatable member are secured to one another along a sealing line having a perimeter, wherein the frame member is secured to the inflatable member inside the perimeter of the sealing line.

5. A foot cuff for applying compressive pressure to a foot of a wearer, the foot cuff comprising:
    an inflatable member including first and second fluid impermeable layers secured to one another to define an inflatable chamber, the inflatable member having a body portion configured to underlie the foot and extend generally between the ball and the heel of the foot and a wing portion extending laterally outward from the body portion, substantially an entirety of a perimeter edge margin of the inflatable member having a rigidity greater than a rigidity of the inflatable member inside the perimeter edge margin; and
    an outer layer,
    wherein the inflatable member directly overlies the outer layer and is secured to the outer layer at the wing portion of the inflatable member, an entirety of the body portion of the inflatable member being free from securement to the outer layer.

6. A foot cuff as set forth in claim 5 wherein the wing portion is secured to the outer layer at discrete locations comprising at least two locations spaced apart along the perimeter edge margin of the inflatable member at the wing portion.

7. A foot cuff as set forth in claim 5 further comprising a frame member secured to the inflatable member for imparting rigidity to the inflatable member in the body portion of the inflatable member.

8. A method of making a foot cuff for applying compressive forces to a foot of a wearer, the method comprising:
    securing a frame member to a perimeter edge margin of an inflatable member having a body portion configured to underlie the foot and extend generally between the ball and the heel of the foot and a wing portion so that the inflatable member at substantially an entirety of the perimeter edge margin is more rigid than the inflatable member inside the perimeter edge margin;
    positioning the inflatable member so that the inflatable member directly overlies an outer layer; and
    securing the inflatable member to the outer layer of the foot cuff at a discrete location at the wing portion of the inflatable member, wherein an entirety of the body portion of the inflatable member is free from direct securement to the outer layer.

9. A method of making a foot cuff for applying compressive forces to a foot of a wearer, the method comprising:
    providing an outer layer;
    providing an inflatable member formed by welding first and second fluid impermeable layers together along a sealing line to define an inflatable chamber, the inflatable member having a perimeter edge margin, wherein the inflatable member has a body portion configured to underlie a foot of the wearer and extend generally between the ball and the heel of the foot, and a wing portion extending laterally outward from the body portion the inflatable member directly overlying the outer layer and being secured to the outer layer at the wing portion of the inflatable member, an entirety of the body portion of the inflatable member being free from direct securement to the outer layer; and providing a frame member on the perimeter edge margin of the inflatable member that has a rigidity greater than a rigidity of the inflatable member, the frame member being formed independently of welding the first and second layers together along the sealing line.

10. A method as set forth in claim 9 wherein providing the frame member comprises forming the frame member separately from the first and second fluid impermeable layers and securing the frame member to the first and second fluid impermeable layers at the perimeter edge margin of the inflatable member.

11. A method as set forth in claim 9 wherein providing the frame member comprises forming at least one of the first and second fluid impermeable layers prior to securing the first and second fluid impermeable layers together along the sealing line with the perimeter edge margin that is thicker than a remainder of said one of the first and second fluid impermeable layers.

12. A method as set forth in claim 9 wherein providing the frame member further comprises forming both of the first and second fluid impermeable layers prior to securing the first and second fluid impermeable layers together along the sealing line with the perimeter edge margin that is thicker than respective remainders of the first and second fluid impermeable layers.

13. A method as set forth in claim 9 wherein providing the frame member includes locating the frame member in a position spaced from the sealing line.

* * * * *